(12) United States Patent  
Masuda et al.

(10) Patent No.: US 8,980,931 B1
(45) Date of Patent: Mar. 17, 2015

(54) METHOD OF EVALUATING PHARMACEUTICAL PREPARATION CONTAINING LULICONAZOLE AND INDEX SUBSTANCE

(71) Applicants: Pola Pharma Inc., Tokyo (JP); Nihon Nohyaku Co., Ltd., Tokyo (JP)

(72) Inventors: Takaaki Masuda, Kanagawa (JP); Hiroshi Yamaguchi, Tokyo (JP)

(73) Assignees: Pola Pharma Inc., Tokyo (JP); Nihon Nohyaku Co., Ltd., Tokyo (JP)

( * ) Notice: Subject to any disclaimer, the term of this patent is extended or adjusted under 35 U.S.C. 154(b) by 0 days.

(21) Appl. No.: 14/263,293

(22) Filed: Apr. 28, 2014

(30) Foreign Application Priority Data

Dec. 12, 2013 (JP) ................................ 2013-256584

(51) Int. Cl.
    *A61K 31/4178* (2006.01)
    *C07D 409/06* (2006.01)
    *G01N 30/02* (2006.01)

(52) U.S. Cl.
    CPC ............ *G01N 30/02* (2013.01); *A61K 31/4178* (2013.01); *G01N 2030/027* (2013.01)
    USPC ....................................... 514/397; 548/315.1

(58) Field of Classification Search
    None
    See application file for complete search history.

(56) References Cited

U.S. PATENT DOCUMENTS

| | | |
|---|---|---|
| 2009/0030059 A1 | 1/2009 | Miki et al. |
| 2009/0076109 A1 | 3/2009 | Miki et al. |
| 2009/0137651 A1 | 5/2009 | Kobayashi et al. |
| 2010/0168200 A1 | 7/2010 | Masuda et al. |
| 2010/0173965 A1 | 7/2010 | Masuda et al. |
| 2010/0204293 A1 | 8/2010 | Masuda et al. |
| 2010/0210702 A1 | 8/2010 | Vontz et al. |
| 2010/0249202 A1 | 9/2010 | Koga et al. |

(Continued)

FOREIGN PATENT DOCUMENTS

| | | | |
|---|---|---|---|
| EP | 0715856 A1 | 6/1996 | |
| EP | 2005958 A1 | 12/2008 | |

(Continued)

OTHER PUBLICATIONS

U.S. Appl. No. 14/347,939, Masuda et al.

(Continued)

*Primary Examiner* — Michael Barker
(74) *Attorney, Agent, or Firm* — Knobbe, Martens, Olson & Bear LLP

(57) ABSTRACT

Disclosed is a method of evaluating stability of a pharmaceutical preparation containing luliconazole. The method includes measuring an amount of production of an SE form of luliconazole represented by following formula (2), an amount of production of a Z form of luliconazole represented by following formula (3) and an amount of production of an amide form of luliconazole represented by following formula (1) after storage under a severe condition or an accelerated condition, and judging that the stability of the pharmaceutical preparation is high if each of the amount of production of the SE form, the amount of production of the Z form and the amount of production of the amide form is not more than 5% by weight with respect to a compounded amount of luliconazole.

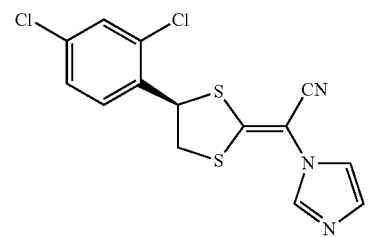

Luliconazole

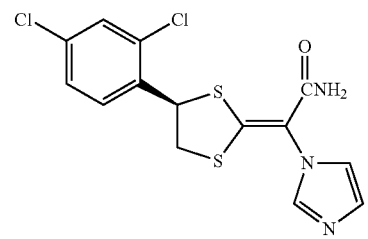

(1)

Amide form

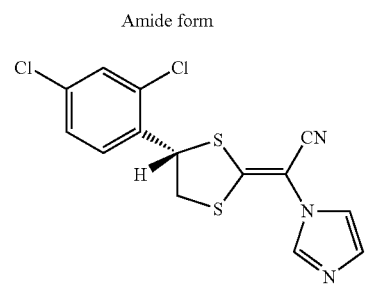

(2)

SE form

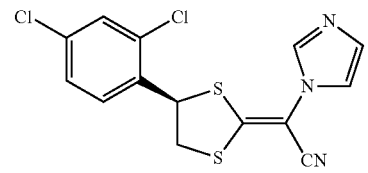

(3)

Z form

3 Claims, No Drawings

(56) References Cited

U.S. PATENT DOCUMENTS

| | | |
|---|---|---|
| 2012/0015997 A1 | 1/2012 | Miki et al. |
| 2012/0022120 A1 | 1/2012 | Kobayashi et al. |
| 2012/0149745 A1 | 6/2012 | Kobayashi et al. |
| 2012/0329845 A1 | 12/2012 | Masuda et al. |
| 2013/0011351 A2 | 1/2013 | Kobayashi et al. |
| 2013/0090365 A1 | 4/2013 | Kubota et al. |
| 2013/0096187 A1 | 4/2013 | Kobayashi et al. |
| 2013/0231379 A1 | 9/2013 | Koga et al. |
| 2014/0080882 A1 | 3/2014 | Masuda et al. |

FOREIGN PATENT DOCUMENTS

| | | |
|---|---|---|
| JP | 2002-114680 A | 4/2002 |
| JP | 2012-202696 | 10/2012 |
| WO | WO 2007/102241 A1 | 9/2007 |
| WO | WO 2007/102242 A1 | 9/2007 |
| WO | WO 2007/102243 A1 | 9/2007 |
| WO | WO 2009/028495 A1 | 3/2009 |
| WO | WO 2009/031642 A1 | 3/2009 |
| WO | WO 2009/031643 A1 | 3/2009 |
| WO | WO 2009/031644 A1 | 3/2009 |
| WO | WO 2014/041708 A1 | 3/2014 |
| WO | WO 2014/041846 A1 | 3/2014 |
| WO | WO 2014/042043 A1 | 3/2014 |
| WO | WO 2014/136282 | 9/2014 |

OTHER PUBLICATIONS

Office Action issued in corresponding Japanese Patent Application No. 2013-256584, on Mar. 11, 2014.

Office Action issued in corresponding Japanese Patent Application No. 2013-256584, on May 7, 2014.

Niwano et al., "Efficacy of NND-502, a novel imidazole antimycotic agent, in experimental models of *Candida albicans* and *Aspergillus fumigatus* infections," *International Journal of Antimicrobial Agents*, vol. 12, pp. 221-228 (1999).

Pola Chemical Industries, Inc., Nihon Nohyaku Co., Ltd., Material regarding luliconazole, Lulicon Cream 1%, and Lulicon Solution 1%, Excerpt (Table of abbreviations and the like, Table of contents, B, C, and E), presumed published before Dec. 12, 2013.

METHOD OF EVALUATING PHARMACEUTICAL PREPARATION CONTAINING LULICONAZOLE AND INDEX SUBSTANCE

CROSS-REFERENCE TO RELATED APPLICATIONS

This application claims the priority benefit of Japan application serial no. 2013-256584, filed on Dec. 12, 2013. The entirety of the above-mentioned patent application is hereby incorporated by reference herein and made a part of this specification.

TECHNICAL FIELD

The present invention relates to a method of evaluating stability of a pharmaceutical preparation containing luliconazole and to an indicator (index substance) which is useful for the method, and the index substance includes an amide form.

BACKGROUND ART

Luliconazole is an antifungal agent which is excellent in the action on fungi. At present, luliconazole is widely used as a pharmaceutical or medicine for tinea pedis and tinea corporis, and it is going to be applied also for the action on tinea unguium as well. Known problems which should be solved in relation to the pharmaceutical preparation of luliconazole include that luliconazole is converted to the stereoisomers such as the SE form or the Z form, and that the crystallization of luliconazole is caused immediately after the application (see, for example, Patent Documents 1 to 6).

PRECEDING TECHNICAL DOCUMENTS

Patent Documents

Patent Document 1: WO2007/102241;
Patent Document 2: WO2007/102242;
Patent Document 3: WO2007/102243;
Patent Document 4: WO2009/31642;
Patent Document 5: WO2009/31643;
Patent Document 6: WO2009/31644.

SUMMARY OF THE INVENTION

Technical Problem

However, nothing is known about the presence of an amide form of the luliconazole represented below. Further, nothing is known at all as well about the fact that the presence or absence of the production of this substance becomes an important problem to select a solvent in the pharmaceutical preparation.

Further, it is considered that this amide form is produced by the addition of water with respect to a cyano group of the luliconazole. However, contrary to the speculation of the presence of the amide form, the amide form is hardly produced even if a luliconazole as an active ingredient undergoes an accelerated test and/or a severe test. Namely, the presence of the amide form is speculated; however, the substance thereof has not been understood. Accordingly, it is difficult to speculate in the stage of manufacturing the pharmaceutical preparation that such a compound may be produced under a storage condition depending on the type of the solvent. Further, as the SE form and the Z form are relatively readily produced by the accelerated test and/or the severe test, the production mechanism of the amide form is considered different from those of the SE form and the Z form.

On the other hand, when a pharmaceutical preparation of luliconazole is manufactured, the present inventors have experienced that a related substance, which is different from the SE form and the Z form, appears depending on the type of the selected solvent. Such recognition has been obtained that the key of the manufacturing of a pharmaceutical preparation of luliconazole is to specify the related substance and clarify the relationship with respect to the pharmaceutical preparation components.

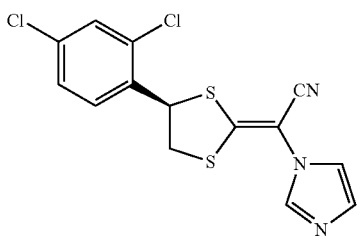

Luliconazole

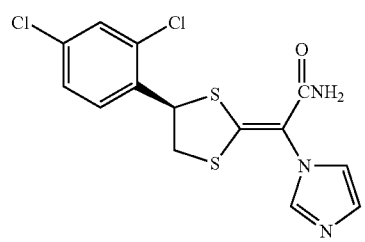

Amide form (1)

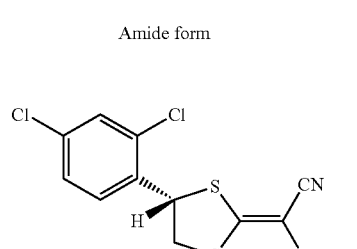

SE form (2)

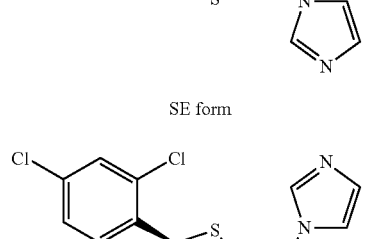

Z form (3)

The present invention has been made in the circumstances as described above, an object of which is to provide a technique to improve the stability of a pharmaceutical preparation containing luliconazole.

Solution to Problem

Taking the foregoing circumstances into consideration, the present inventors have repeatedly performed diligent researches and efforts in order to seek a technique to improve the stability of a pharmaceutical preparation containing luliconazole. As a result, it has been found out that the time-dependent production of an amide form is present as a factor of inhibiting the stability of a pharmaceutical preparation containing luliconazole. That is, in a luliconazole pharmaceutical preparation, it is possible that an amide form may be produced depending on the types of constituent components of the preparation, independently from the production of the SE form and the Z form. It has been found out that more stable pharmaceutical preparation containing luliconazole may be obtained by adding an amount of production of such an amide form as an stability index together with an amount of production of the SE form and the Z form of luliconazole to evaluate the stability.

That is, the present invention is as follows.

<1> A method of evaluating stability of a pharmaceutical preparation containing luliconazole, comprising:
  measuring an amount of production of an SE form of luliconazole represented by following formula (2), an amount of production of a Z form of luliconazole represented by following formula (3) and an amount of production of an amide form of luliconazole represented by following formula (1) after storage under a severe condition or an accelerated condition, and judging that the stability of the pharmaceutical preparation is high if each of the amount of production of the SE form, the amount of production of the Z form and the amount of production of the amide form is not more than 5% by weight with respect to a compounded amount of luliconazole.

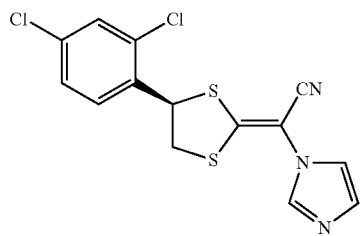

Luliconazole

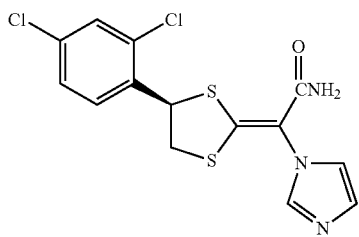

Amide form (1)

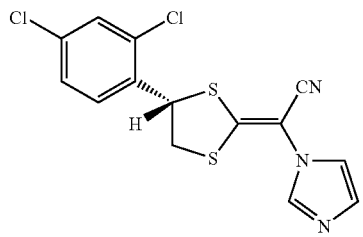

SE form (2)

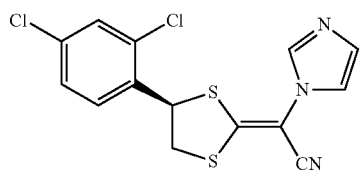

Z form (3)

<2> The evaluation method according to <1>, wherein each of the amount of production of the SE form, the amount of production of the Z form and the amount of production of the amide form is not more than 0.2% by weight with respect to the compounded amount of luliconazole.

<3> The evaluation method according to <1> or <2>, wherein the severe condition and the accelerated condition are 60° C. for 3 weeks and 40° C. for 6 months, respectively.

<4> The evaluation method according to any of <1> to <3>, wherein the pharmaceutical preparation containing luliconazole comprises one or more of a component selected from polyhydric alcohol or ether thereof, dibasic acid ester, aromatic alcohol, ketone, triglyceride and heterocyclic solvent.

<5> The evaluation method according to <4>, wherein
  the polyhydric alcohol or the ether thereof is selected from propylene glycol, polyethylene glycol, 1,3-butanediol, diethylene glycol monoethyl ether, diethylene glycol diethyl ether and polypropylene glycol;
  the dibasic acid ester is selected from diethyl adipate, diisopropyl adipate and propylene carbonate;
  the aromatic alcohol is benzyl alcohol;
  the ketone is acetone or methyl ethyl ketone;
  the triglyceride is medium chain fatty acid triglyceride or olive oil; and
  the heterocyclic solvent is N-methyl-2-pyrrolidone or N-ethyl-2-pyrrolidone.

<6> A pharmaceutical medicament preparation, comprising:
  1) luliconazole; and
  2) one or more components selected from polyhydric alcohol or ether thereof, dibasic acid ester, aromatic alcohol, ketone, triglyceride and heterocyclic solvent, wherein
  upon measurement of an amount of production of an SE form of luliconazole represented by following formula (2), an amount of production of a Z form of luliconazole represented by following formula (3) an amount of production of an amide form of luliconazole represented by following formula (1) by storage under a severe condition and an accelerated condition, each of the amount of production of the SE form, the amount of production of the Z form and the amount of production of the amide form is not more than 5% by mass with respect to a compounded amount of luliconazole.

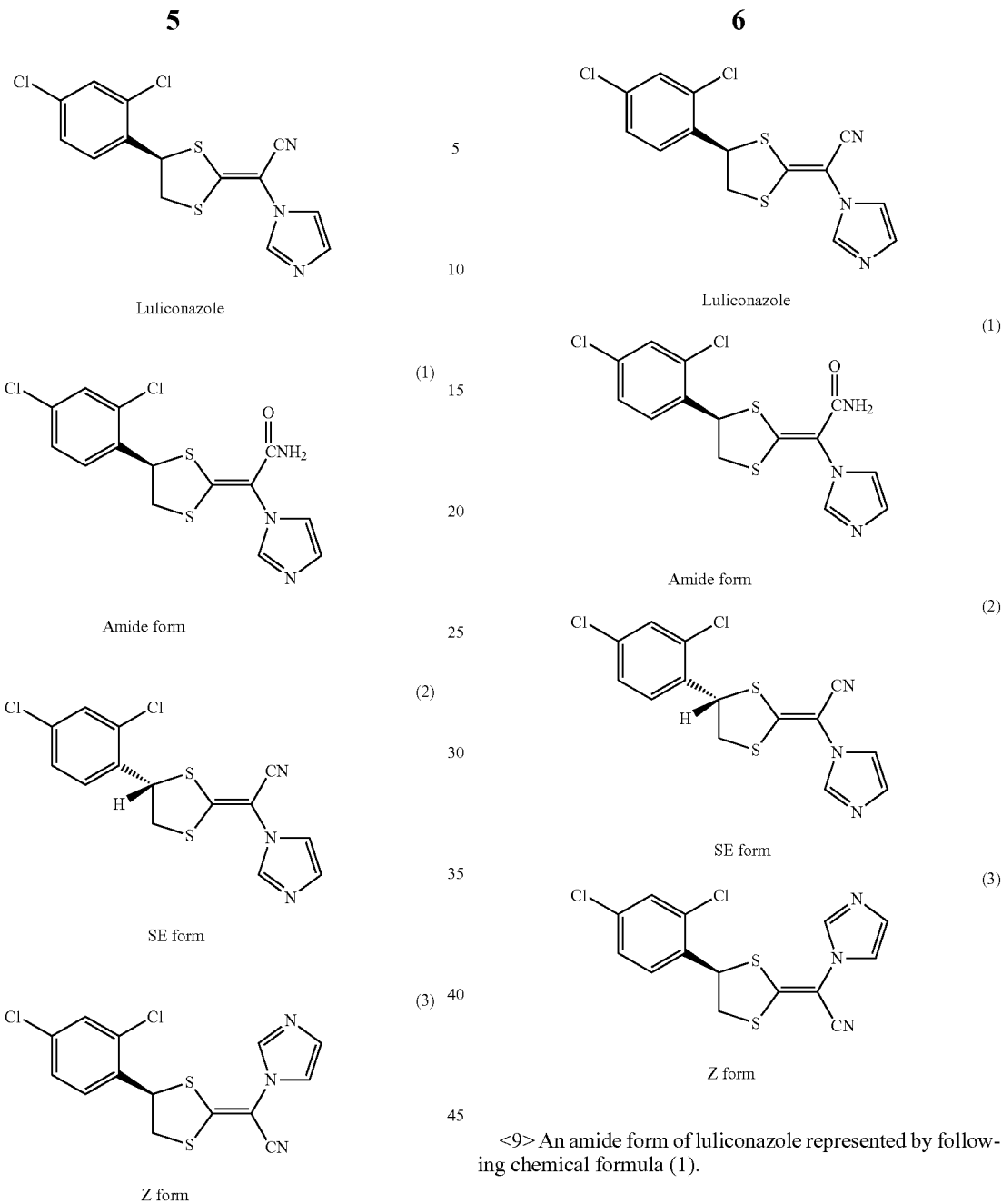

<7> The pharmaceutical medicament preparation according to <6>, wherein each of the amount of production of the SE form, the amount of production of the Z form and the amount of production of the amide form after storage under the severe condition and the accelerated condition is not more than 0.2% by mass with respect to the compounded amount of luliconazole.

<8> An index substance of the stability of a pharmaceutical preparation containing luliconazole, the index substance including an amide form of the luliconazole indicated in following formula (1), wherein the index substance of the stability complements the evaluation of the stability that uses an SE form of luliconazole represented by following formula (2) and a Z form of luliconazole represented by following formula (3) as index substances.

<9> An amide form of luliconazole represented by following chemical formula (1).

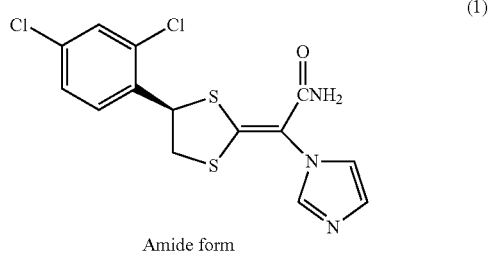

Advantageous Effects of Invention

The present invention can provide a technique to improve the stability of a pharmaceutical preparation containing luliconazole.

DESCRIPTION OF EMBODIMENTS

<1> Evaluation Method of the Present Invention

The present invention relates to the method of evaluating the stability of a pharmaceutical preparation containing luliconazole. The method includes measuring an amount of production of the SE form of luliconazole of the above-indicated structure, an amount of production of the Z form of luliconazole of the above-indicated structure and an amount of production of the amide form of luliconazole of the above-indicated structure after storage under a severe condition or an accelerated condition, and judging that the stability of the pharmaceutical preparation is high if each of the amount of production of the SE form, the amount of production of the Z form and the amount of production of the amide form is small.

The severe condition herein refers to a storage condition at 60° C. for 3 weeks, and the accelerated condition herein refers to a storage condition at 40° C. for 6 months. The stability of a pharmaceutical preparation containing luliconazole has shown very good consistency between the severe condition and the accelerated condition. Accordingly, either of the conditions can be used. Further, the storage at 40° C. for 6 months is known as a condition substitutable for the condition at a room temperature for 3 years in an application for manufacturing approval of a pharmaceutical.

The amide form ([R-(E)]-α-[4-(2,4-dichlorophenyl)-1,3-dithiolan-2-ylidene]-1H-imidazole-1-acetamide) of luliconazole is very hardly produced by decomposition and the like of a luliconazole active ingredient, and is hardly produced by the severe test or the accelerated test of the luliconazole as the active ingredient. It is known that water is usually readily added to a cyano group by an acid or a base and the amide form is thereby produced. However, this generality is not applicable in the case of luliconazole, for the following reason. It is considered that a cyano group is stable because of a conjugated structure thereof continuing from a dithiolane ring to a side chain double bond, an imidazolyl group attached to the side chain double bond and a substituted phenyl group attached to the dithiolane ring. Therefore, whether each of an amount of production of the SE form and an amount of production of the Z form under the accelerated condition or the severe condition is large or small has been used as an index of the stability of luliconazole.

However, in the process of researching the manufacturing of the pharmaceutical preparation, the present inventors have recognized that the amide form is produced after the storage of the pharmaceutical under the accelerated condition or the severe condition by being affected by components blended therein, independently from the amount of production of the SE form and the amount of production of the Z form under the accelerated condition or the severe condition, and have found out that, in a case where the component to be blended is changed, an amount of production of the amide form should be used as an index of the stability in addition to an amount of production of the SE form and an amount of production of the Z form.

The amide form of luliconazole is produced by treating luliconazole together with water in the presence of a metal catalyst such as copper, iridium, alumina and hydroxyapatite. Alternatively, the amide form is also obtained by making an acid or an alkali to act on luliconazole in water-containing ethanol. However, it is preferred that a catalyst as mentioned above is present. The amide form thus obtained is purified by means of, for example, the chromatography such as silica gel column chromatography, octadecyl modified silica gel column chromatography or the like and/or the recrystallization from a mixture solution of ethyl acetate and normal hexane, ethanol, isopropanol or the like, and the amide form is provided as the index substance. Since the amide form of luliconazole is, as mentioned above, a substance which is difficult to produce under normal conditions, it is preferable to undergo a reaction under the presence of a catalyst as mentioned above. Even if the reaction is under the presence of such a catalyst, a purification process by means of column chromatography and the like is required as the ratio of conversion to the amide form is low. As for the index substance, it is preferable that the purity is not less than 90%.

Such a component can be confirmed by means of HPLC. When the related substance of luliconazole is confirmed, a chiral normal phase column is used in many cases in order to distinguish luliconazole and the isomer such as the SE form or the Z form. However, the amide form represented by the chemical formula (1) is hardly detected under the elution condition for the chiral normal phase column. Therefore, it is preferable to perform the investigation under such a condition that a reverse phase column, which is based on the use of cation-capturing counterion such as alkylsulfonate or the like, is used. Such an analysis condition is preferably exemplified by the following. Under such a condition, it is also possible to detect main related substances such as the SE form, the Z form or the like together with luliconazole. By adopting such a method, it is possible to simultaneously measure the three index substances of the evaluation method of the present invention. Such three index substance, namely the SE form, the Z form and the amide form, can be measured by means of HPLC with a following condition.

Column: Inertsil ODS-2 4.6×150 mm, column temperature: 40° C., mobile phase: solution of 0.13% sodium undecan-1-sulfonate mixture (water/acetonitrile/acetic acid (100) (54:45:1, v/v/v)), flow rate: 1.0 mL/min., detection: 295 nm.

The subject of the evaluation method of the present invention is a pharmaceutical preparation containing luliconazole. When a pharmaceutical preparation of luliconazole is prepared, the amide form represented by the chemical formula (1) is produced during the storage at a high temperature of 40 to 60° C. depending on the type of the selected solvent. The antifungal activity of the amide form itself is low. Therefore, the production of the amide form results in the decrease in the activity of the pharmaceutical preparation.

It has been grasped that the addition of polyhydric alcohol such as 1,3-butanediol is the factor of the production of such an amide form. Other than polyhydric alcohol, it is possible to exemplify, for example, dibasic acid ester such as diethyl adipate, aromatic alcohol such as benzyl alcohol, ketone such as acetone and methyl ethyl ketone, triglyceride such as medium chain fatty acid triglyceride, and heterocyclic solvent such as N-methyl-2-pyrrolidone as the solvent with which the amide form may be produced.

If such an index substance is increased in the prepared pharmaceutical preparation, an amount of production of the amide form as described above can be changed by separating the solvent and substituting the solvent which may cause production of an amide form such as polyhydric alcohol with another solvent. Thus, it is possible to secure the stability of the pharmaceutical preparation.

The following guideline on the stability of this pharmaceutical preparation can be exemplified. That is, an amount of production of the amide form is preferably not more than 10% by mass, more preferably not more than 5% by mass, much more preferably not more than 1% by mass, and still much more preferably not more than 0.5% by mass with respect to a compounded amount of luliconazole after the storage at 40° C. for 6 months (accelerated condition) or the storage at 60° C. for 3 weeks (severe condition), for the following reason.

That is, within this range, substantially no influence is exerted on the activity of the pharmaceutical preparation. Furthermore, if an amount of production is not more than 0.2% by mass, the degree of contribution as a related substance is small. Any active pharmaceutical ingredient-related substance within such an amount range is not classified into the related substance according to the Pharmaceutical Affairs Law in Japan.

Further, the content of the amide form represented by the chemical formula (1) as described above can be measured to evaluate a product, and thus, the evaluation can guarantee the quality of the product. In such a case, it is preferable that the operation for measuring the content of the amide form represented by the chemical formula (1) is incorporated into the production step concerning the quality of the product. The production step concerning the quality of the product is preferably exemplified, for example, by the step of dissolving luliconazole in the solvent or the like. It is also preferable that the operation for measuring the content of the amide form is incorporated into the storage step for the produced product.

It is also preferable that an amount of production of the SE form and/or an amount of production of the Z form are/is also measured together with the above measuring step by means of a chiral column to control the production thereof in order to improve the quality of the product, for the following reason. That is, in particular, since the production mechanism of the SE form and the production mechanism of the Z form are different from each other and also different from the production mechanism of the amide form, only suppressing the production of any one of the SE form, Z form and amide form could lead to an increase in the other related substances.

The SE form or the Z form can be measured by means of HPLC under a following HPLC condition. In a final product, each of the amide form represented by the chemical formula (1), the SE form represented by the chemical formula (2) and the Z form represented by the chemical formula (3) is preferably not more than 5% by mass, more preferably 1% by mass, much more preferably not more than 0.5% by mass, and still much more preferably not more than 0.2% by mass with respect to a compounded amount of luliconazole. Such a pharmaceutical medicament preparation is a preferable mode of the pharmaceutical medicament preparation of the present invention. In such a mode, long-term stability can be secured.

<Measurement Condition of SE Form and Z Form>

HPLC condition: Column: CHIRALCEL OD-RH 4.6×150 mm, column temperature: 35° C., mobile phase: mixture of methanol/1.8% potassium hexafluorophosphate solution (83:17, v/v)), flow rate: 0.56 mL/min., detection: 295 nm.

Polyhydric alcohol is exemplified as a solvent that is used for a pharmaceutical preparation containing luliconazole. In general, 1,3-butanediol, propylene glycol, polyethylene glycol, polypropylene glycol, polyoxyethylene-polyoxypropylene glycol and glycerin can be exemplified as the polyhydric alcohol. Alkyl ethers having 1 to 4 carbon atoms can be preferably exemplified as an ether form thereof. Specifically, diethylene glycol monoethyl ether, diethylene glycol diethyl ether and the like can be exemplified.

The degree of polymerization of the polymer is usually about 2 to 50, and preferably 3 to 30.

Among the above, 1,3-butanediol usually has an intense tendency to facilitate the production of an amide form. Even in the case of polyhydric alcohol, for example, polyethylene glycol and polypropylene glycol have a weak tendency thereof, and rather have a tendency of suppressing the production of an amide form compared with the 1,3-butanediol. Therefore, when the amide form is considerably produced in a pharmaceutical preparation containing 1,3-butanediol, the production of the amide form can be suppressed by substituting 1,3-butanediol with polyethylene glycol and/or polypropylene glycol.

In order to achieve the suppression as described above, in the case of polyethylene glycol, it is possible to exemplify that polyethylene glycol is contained preferably by 20 to 50% by mass, and more preferably by 28 to 35% by mass with respect to the total amount of the pharmaceutical preparation. On the other hand, polypropylene glycol is contained preferably by 15 to 40% by mass and more preferably by 17 to 25% by mass with respect to the total amount of the pharmaceutical preparation, for the following reason. That is, if the content is excessively large, the compatibility with respect to luliconazole is deteriorated in some cases. If the content is excessively small, the effect to suppress the amide form is not recognized. When the construction as described above is used, then it is possible to suppress the production of the amide form, and an amount of production of the amide form can be suppressed to be not more than 10% by mass, more preferably not more than 5% by mass, much more preferably not more than 1% by mass, still much more preferably not more than 0.5% by mass and yet more preferably not more than 0.2% even under the accelerated condition at 40° C. for 6 months or under the severe condition at 60° C. for 3 weeks. As such, polyhydric alcohol or ether thereof comprises a component that facilitates the production of an amide form and a component that suppresses the production of an amide form; therefore, it is necessary to confirm the stability by means of the evaluation method of the present invention.

The polyhydric alcohol that is used for a pharmaceutical preparation containing luliconazole to which the evaluation method of the present invention is applied, can be preferably exemplified by a polyhydric alcohol selected from propylene glycol, polyethylene glycol, 1,3-butanediol, diethylene glycol monoethyl ether, diethylene glycol diethyl ether and polypropylene glycol. Polyhydric alcohol is contained preferably by 5 to 70% by mass with respect to the total amount of the pharmaceutical preparation.

A single general concept including a component facilitating the production of an amide form and a component suppressing the production thereof can be exemplified by a solvent.

A solvent that can be used for a pharmaceutical preparation containing luliconazole can be preferably exemplified, other than polyhydric alcohol, for example, dibasic acid ester such as propylene carbonate, diethyl adipate, diisopropyl adipate and diethyl sebacate; aromatic alcohol such as benzyl alcohol and phenethyl alcohol; ketone such as acetone and methyl ethyl ketone; triglyceride such as medium chain fatty triglyceride and olive oil; or heterocyclic solvent such as N-methyl-2-pyrrolidone, N-ethyl-2-pyrrolidone, N-propyl-2-pyrrolidone, N-butyl-2-pyrrolidone and pyrrolidone carboxylate.

In particular, dibasic acid ester is preferably selected from diethyl adipate, diisopropyl adipate and propylene carbonate; benzyl alcohol is preferable as aromatic alcohol; N-methyl-2-pyrrolidone or N-ethyl-2-pyrrolidone is particularly preferable as the heterocyclic solvent; acetone or methyl ethyl ketone is preferable as ketone; and medium chain fatty acid triglyceride or olive oil is preferable as triglyceride. A Solvent such as dibasic acid ester, aromatic alcohol, ketone, triglyceride and heterocyclic solvent is contained preferably by 1 to 30% by mass with respect to the total amount of the pharmaceutical preparation.

<2> Pharmaceutical Preparation of the Present Invention

The pharmaceutical medicament preparation of the present invention is a pharmaceutical medicament preparation containing: 1) luliconazole; and 2) one or more components selected from polyhydric alcohol or ether thereof, dibasic acid ester, aromatic alcohol, ketone, triglyceride and heterocyclic solvent. The pharmaceutical medicament preparation is characterized by that an amount of production of the SE form indicated above, an amount of production of the Z form of luliconazole indicated above and an amount of production of the amide form of luliconazole indicated above after storage under the severe condition or the accelerated condition are measured, and each of the amount of production of the SE form, the amount of production of the Z form and the amount of production of the amide form is not more than 5% by mass with respect to the compounded amount of luliconazole.

Luliconazole can be synthesized according to, for example, a method described in Japanese Patent Application Laid-Open Publication No. 60 (1985)-218387. That is, 1-cyano-methyl imidazole and carbon disulfide are reacted to obtain a compound (III) which is subsequently reacted with a compound of a general formula (II) having a leaving group to thereby obtain a compound represented by a general formula (1) as follows. As the leaving group, for example, a methanesulfonyloxy group, a benzenesulfonyloxy group, a p-toluenesulfonyloxy group, a halogen atom and the like can be preferably exemplified.

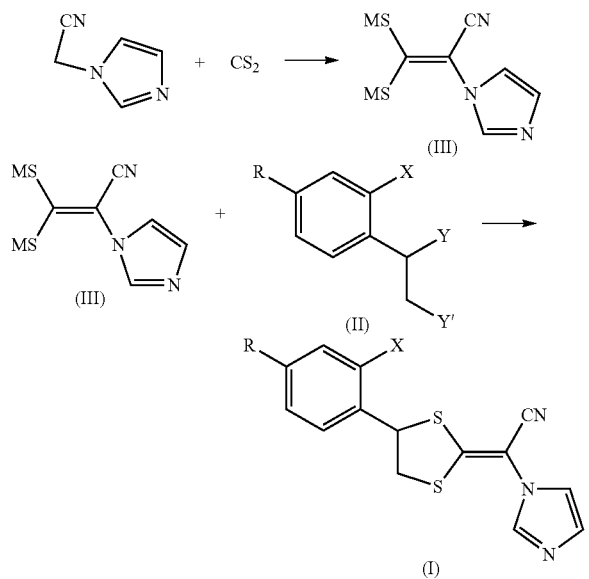

In the formula, Y and Y' represent the leaving group such as a methanesulfonyloxy group, a benzenesulfonyloxy group, a p-toluenesulfonyloxy group or a halogen atom, and M represents alkali metal. R and X represent Cl.

The content of luliconazole in the pharmaceutical medicament preparation of the present invention is preferably 0.1 to 20% by mass, more preferably 0.5 to 15% by mass, and much more preferably 1 to 10% by mass.

Such a pharmaceutical preparation preferably contains: polyhydric alcohol or the ether thereof selected from propylene glycol, polyethylene glycol, 1,3-butanediol, diethylene glycol monoethyl ether, diethylene glycol diethyl ether and polypropylene glycol; dibasic acid ester selected form diethyl adipate, diisopropyl adipate and propylene carbonate; benzyl alcohol as aromatic alcohol; N-methyl-2-pyrrolidone or N-ethyl-2-pyrrolidone as a heterocyclic solvent; acetone or methyl ethyl ketone as ketone; and medium chain fatty acid triglyceride or olive oil as triglyceride. The pharmaceutical preparation containing such a composition is characterized by that the amide form is controlled preferably by not more than 5% by mass, more preferably by not more than 1% by mass, much more preferably by not more than 0.5%, and still much more preferably by not more than 0.2% by mass after storage under the accelerated condition or the severe condition with respect to a compounded amount of luliconazole. The pharmaceutical medicament preparation of the present invention is characterized by that, in addition to the amide form, each of the SE form and the Z form is controlled preferably by not more than 5% by mass, more preferably by not more than 1% by mass, much more preferably by not more than 0.5%, and still much more preferably by not more than 0.2% by mass after storage under the accelerated condition or the severe condition. Such a pharmaceutical medicament preparation is obtained as a product of the evaluation method of the pharmaceutical medicament preparation of the present invention.

The pharmaceutical preparation of the present invention can be manufactured by appropriately adding, in addition to luliconazole and the solvents described above, other solvents, colorants, antioxidants, chelating agents, emulsifying and dispersing agents, solubilizing agents such as polyvinyl pyrrolidone, disintegrating agents, excipients, binding agents, coating agents, flavoring agents, and stabilizers such as lactic acid, and by treating the foregoing components in accordance with an ordinary method.

The pharmaceutical medicament preparation of the present invention is preferably used to treat or cure the disease caused by any fungus or prevent the deterioration of the disease by utilizing the characteristic of luliconazole. The disease caused by any fungus can be exemplified by tinea pedis such as athlete's foot, tinea corporis such as candidiasis and tinea versicolor, and trichophytosis of hard keratin portion such as tinea unguium. It is especially preferable to use the pharmaceutical medicament preparation of the present invention for treating the disease of the hard keratin portion such as tinea unguium, because the effect thereof is remarkable. The effect of the pharmaceutical medicament preparation of the present invention is expressed on the nail especially preferably. However, the effect is also exerted on any ordinary dermatomycosis. Therefore, the pharmaceutical medicament preparation, which is directed to the dermatomycosis and which fulfills the construction of the present invention, also belongs to the technical scope of the present invention. The dermatomycosis as described above can be exemplified, for example, by the tinea pedis and the trichophytosis of the propagation in horny substance type appearing, for example, in the heel and being included in the tinea pedis. As for the dermatomycosis described above, it is preferable to make the application to the trichophytosis of the propagation in horny substance type on which any ordinary agent or drug hardly exerts the effect, because the effect of the present invention remarkably arises.

The mode of use can be appropriately selected while considering, for example, the body weight, the age, the sexuality, and the symptoms or condition of the patient. However, in the case of an adult, it is preferable to administer luliconazole in an amount of 0.01 to 1 g per day in ordinary cases. An amount of use of luliconazole ordinarily used for a disease caused by any fungus can be used as a reference.

For example, in the case of any preparation for external use, it is possible to exemplify the application in an appropriate amount to the disease portion once or several times a day. It is preferable that the treatment as described above is performed every day. In particular, in the case of the tinea unguium, luliconazole as the active ingredient, which is in an amount that cannot be brought about by any ordinary pharmaceutical preparation, can be transferred into the nail. Accordingly, the tinea unguium can be cured by means of only the external administration without taking any antifungal agent for a long period of time. Further, the recurrence and the reinfection cause great problems in relation to the tinea unguium. However, it is possible to avoid the recurrence and the reinfection as described above by administering the pharmaceutical medicament preparation of the present invention for 1 week to 2 weeks after the quietness of symptoms. In such a mode, the pharmaceutical medicament preparation of the present invention has the preventive effect.

<3> Index Substance of the Present Invention

The index substance of the present invention is an index substance of the stability of a luliconazole pharmaceutical preparation, and includes the amide form of luliconazole of the above-indicated structure.

The index substance of the stability complements the evaluation of the stability that uses the SE form of luliconazole and the Z form of luliconazole as index substances.

The wording "complement the evaluation of the stability" means that the index substance of the present invention can be used as an index substance of the stability of a luliconazole pharmaceutical preparation together with the SE form of luliconazole and the Z form of luliconazole.

EXAMPLES

The present invention will be explained in further detail below as exemplified by Examples.

Example 1

One kilogram (1 kg) of luliconazole was dissolved in a solution of ethanol containing 10% water, and 10 g of silica gel was added thereto, followed by being heated and refluxed for 1 hour. After cooling, silica gel was filtrated off. An obtained filtrate was concentrated, followed by being purified by means of silica gel column chromatography to obtain 46.41 g of crude amide form product. This product was recrystallized three times from ethanol, and 2.6 g of purified product was obtained. The characteristic values thereof were as follows.

$^1$H-NMR (CDCl$_3$, ppm): 3.617 (dd, 1H), 3.639 (dd, 1H), 5.554 (dd, 1H), 6.993 (s, 1H), 7.231 to 7.311 (m, 2H), 7.447 to 7.664 (m, 3H); m.p.: 238 to 244° C.

Example 2

Luliconazole pharmaceutical preparation 1 was manufactured in accordance with a formulation shown below. That is, formulation components were heated, stirred, and solubilized, followed by being stirred and cooled to room temperature to obtain the luliconazole pharmaceutical preparation. The luliconazole pharmaceutical preparation was stored under a temperature condition at 60° C. for 3 weeks, and the pharmaceutical preparation after storage was confirmed by means of the HPLC method. As a result, three peaks were confirmed other than the peak of luliconazole, and compounds corresponding to these peaks were purified by column chromatography, and the structures thereof were determined by NMR and mass analysis. The amide form was produced in the largest amount. That is, according to this fact, it is confirmed that the amide form is the important related substance depending on the system.

HPLC condition: column: Inertsil ODS-2 4.6×150 mm, column temperature: 40° C., mobile phase: solution of 0.13% sodium undecan-1-sulfonate mixture (water/acetonitrile/acetic acid (100) (54:45:1, v/v/v)), flow rate: 1.0 mL/min., detection: 295 nm.

Further, the contents of the SE form and the Z form were measured by means of HPLC with the following HPLC condition. Column: CHIRALCEL OD-RH 4.6×150 mm, column temperature: 35° C., mobile phase: mixture of methanol/1.80 potassium hexafluorophosphate solution (83:17, v/v)), flow rate: 0.56 mL/min., detection: 295 nm.

TABLE 1

| Component | % by mass |
| --- | --- |
| Luliconazole | 1 |
| Diisopropyl adipate | 5 |
| Benzyl alcohol | 4 |
| Polyethylene glycol 400 | 30 |
| Ethanol | 60 |

<Related substance>

| Peak | Result of identification | Peak area ratio with respect to peak of luliconazole (%) |
| --- | --- | --- |
| Peak 1 | SE form | 0.4 |
| Peak 2 | Z form | 0.1 |
| Peak 3 | amide form | 1.2 |

Example 3

Pharmaceutical preparations 2 and 3 were manufactured in the same manner as in Example 2. The amide form was measured therefor in the same manner as described above after the storage at 60° C. for 3 weeks as well. Results are shown in Table 2. Accordingly, it is confirmed that 1,3-butanediol is the factor of the production of the amide form. In this way, it is confirmed that the amide form can be also used as the index to discriminate the factor to suppress the stability.

TABLE 2

| Formulation component | Pharmaceutical preparation 2 (% by mass) | Pharmaceutical preparation 3 (% by mass) |
| --- | --- | --- |
| Luliconazole | 1 | 1 |
| Polypropylene glycol* | | 20 |
| Benzyl alcohol | 4 | 4 |
| Diisopropyl adipate | 5 | 5 |
| 1,3-Butanediol | 30 | |
| Water | 30 | 30 |
| Ethanol | 30 | 40 |
| Amount of production of amide form | 0.86 | 0.32 |
| Amount of production of SE form | 0.38 | 0.44 |
| Amount of production of Z form | 0.12 (% by mass) | 0.08 (% by mass) |

*Average molecule weight was 2000

Example 4

Pharmaceutical preparation 4 was manufactured in accordance with a formulation shown below. Also in this case, it is confirmed that the production of the amide form is suppressed under a storage condition at 60° C. for 3 weeks. In relation thereto, it is considered that this is caused by the addition of polyethylene glycol 400. Accordingly, it is considered that polyethylene glycol has the action of suppressing the production of the amide form as that of polypropylene glycol.

TABLE 3

| Formulation component | (% by mass) |
| --- | --- |
| Luliconazole | 5 |
| Propylene carbonate | 5 |
| Benzyl alcohol | 2 |
| Lactic acid | 4 |
| Polyethylene glycol 400 | 20 |
| Diethyl adipate | 24 |
| Polyvinylpyrrolidone | 0.25 |
| Ethanol | 39.75 |
| Amount of production of amide form | 0.02 |
| Amount of production of SE form | 0.39 |
| Amount of production of Z form | 0.05 (% by mass) |

While the invention has been described in detail and with reference to specific embodiments thereof, it will be apparent to one skilled in the art that various changes and modifications can be made therein without departing from the spirit and scope thereof.

INDUSTRIAL APPLICABILITY

The present invention can be applied, for example, to the design of a pharmaceutical preparation of luliconazole and the evaluation of the pharmaceutical preparation.

What is claimed is:

1. A pharmaceutical medicament preparation, comprising:
   1) luliconazole; and
   2) polyhydric alcohol or ether thereof and dibasic acid ester, wherein
   upon measurement of an amount of production of an SE form of luliconazole represented by following formula (2), an amount of production of a Z form of luliconazole represented by following formula (3) and an amount of production of an amide form of luliconazole represented by following formula (1) by storage under a severe condition and an accelerated condition, each of the amount of production of the SE form, the amount of production of the Z form and the amount of production of the amide form is not more than 5% by mass with respect to a compounded amount of luliconazole.

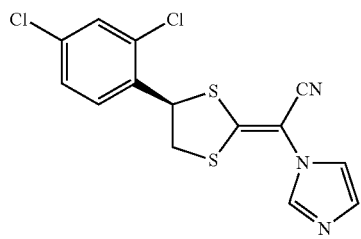

Luliconazole

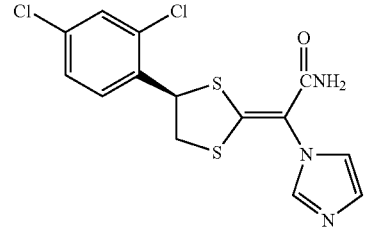

Amide form (1)

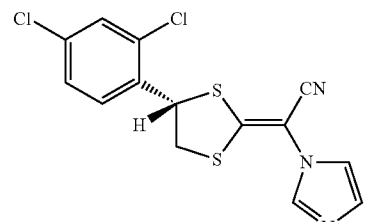

SE form (2)

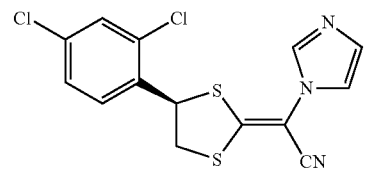

Z form (3)

2. The pharmaceutical medicament preparation according to claim 1, wherein each of the amount of production of the SE form, the amount of production of the Z form and the amount of production of the amide form after storage under the severe condition and the accelerated condition is not more than 0.5% by mass with respect to the compounded amount of luliconazole.

3. The pharmaceutical medicament preparation according to claim 1,
   wherein polyhydric alcohol or ether thereof is selected from propylene glycol, polyethylene glycol, 1,3-butanediol, diethylene glycol monoethyl ether, diethylene glycol diethyl ether and polypropylene glycol; and dibasic acid ester is selected from diethyl adipate, diisopropyl adipate and propylene carbonate.

* * * * *